United States Patent
Ahire et al.

(10) Patent No.: US 9,062,065 B2
(45) Date of Patent: Jun. 23, 2015

(54) PROCESS FOR PREPARATION OF DARUNAVIR AND DARUNAVIR ETHANOLATE OF FINE PARTICLE SIZE

(75) Inventors: Vijay Ahire, Pune (IN); Sachin Sasane, Pune (IN); Amol Deshmukh, Pune (IN); Krishnat Kumbhar, Pune (IN); Akshat Bhatnagar, Pune (IN); Devendra Verma, Pune (IN); Rajesh Vyas, Pune (IN); Girij Pal Singh, Pune (IN); Nandu Bhise, Pune (IN)

(73) Assignee: LUPIN LIMITED, Mumbai, Maharashtra (IN)

( * ) Notice: Subject to any disclaimer, the term of this patent is extended or adjusted under 35 U.S.C. 154(b) by 239 days.

(21) Appl. No.: 13/505,148

(22) PCT Filed: Nov. 1, 2010

(86) PCT No.: PCT/IN2010/000714
§ 371 (c)(1),
(2), (4) Date: Apr. 30, 2012

(87) PCT Pub. No.: WO2011/051978
PCT Pub. Date: May 5, 2011

(65) Prior Publication Data
US 2012/0237770 A1     Sep. 20, 2012

(30) Foreign Application Priority Data

Oct. 30, 2009  (IN) .......................... 1303/KOL/2009
Sep. 9, 2010  (IN) .......................... 1000/KOL/2010

(51) Int. Cl.
*C07D 493/04* (2006.01)
*B02C 23/02* (2006.01)
*C07C 29/00* (2006.01)

(52) U.S. Cl.
CPC ......... *C07D 493/04* (2013.01); *Y10T 428/2982* (2015.01); *C07C 29/00* (2013.01)

(58) Field of Classification Search
None
See application file for complete search history.

(56) References Cited

U.S. PATENT DOCUMENTS

| 5,843,946 A | 12/1998 | Vazquez et al. |
| 6,068,858 A * | 5/2000 | Liversidge et al. ........... 424/489 |
| 6,248,775 B1 | 6/2001 | Vazquez et al. |
| 6,919,465 B2 | 7/2005 | Ghosh et al. |
| 7,700,645 B2 | 4/2010 | Vermeersch et al. |
| 2007/0060642 A1 | 3/2007 | Goyvaerts et al. |

FOREIGN PATENT DOCUMENTS

| WO | WO 03/022853 | 3/2003 |
| WO | WO 2005/095410 | 10/2005 |
| WO | WO 2008/055970 | 5/2008 |
| WO | WO 2009/013356 | 1/2009 |
| WO | WO 2010/023322 | 3/2010 |
| WO | WO2011/048604 | * 9/2010 |
| WO | WO 2011/048604 | 4/2011 |
| WO | WO 2011/092687 | 8/2011 |

OTHER PUBLICATIONS

Ghosh et al., "Synthesis and Optical Resolution of High Affinity $P_2$-Ligands for HIV-1 Protease Inhibitors", *Tetrahedron Letters*, vol. 36, No. 4, pp. 505-508.
Ghosh et al., "Nonpeptidal $P_2$ Ligands for HIV Protease Inhibitors: Structure-Based Design, Synthesis, and Biological Evaluation", *J. Med. Chem.*, vol. 39, 1996, pp. 3278-3290.
Ghosh et al., "Stereoselective Photochemical 1,3-Dioxolane Addition to 5-Alkoxymethyl-2(5H)-furanone: Synthesis of Bistetrahydrofuranyl Ligand for HIV Protease Inhibitor UIC-94017 (TMC-114)", *J. Org. Chem.*, vol. 69, 2004, pp. 7822-7829.
International Search Report for International Application No. PCT/IB2010/000714 mailed May 24, 2011.
"Prezista EPAR—Scientific Discussion", Internet Citation, 2006, pp. 1-56.
Surleraux et al., "Discovery and Selection of TMC114, a Next Generation HIV-1 Protease Inhibitor", *J. Med. Chem.*, vol. 48, 2005, pp. 1813-1822.
Van Gyseghem et al., "Co-administration of darunavir and a new pharmacokinetic booster: Formulation strategies and evaluation in dogs", *European Journal of Pharmaceutical Sciences*, vol. 41, 2010, pp. 193-200.

* cited by examiner

*Primary Examiner* — Ronak Patel
(74) *Attorney, Agent, or Firm* — Merchant & Gould P.C.

(57) ABSTRACT

The present invention provides a novel process for preparation of darunavir that involves reduction of [(1S,2R)-3-[[(4-nitrophenyl)sulfonyl](2-methylpropyl)amino]-2-hydroxy-1-(phenylmethyl)propyl]carbamic acid (3R,3aS,6aR)-hexahydrofuro[2,3-b]furan-3-yl ester, of formula (5). The present invention also provides darunavir ethanolate of particle size wherein $d_{0.9}$ is less than 130 μm, $d_{0.5}$ is less than 30 μm, $d_{0.1}$ is less than 10 μm and process for its preparation.

6 Claims, No Drawings

PROCESS FOR PREPARATION OF DARUNAVIR AND DARUNAVIR ETHANOLATE OF FINE PARTICLE SIZE

This application is a National Stage Application of PCT/IN2010/000714, filed 1 Nov. 2010, which claims benefit of Serial No. 1000/KOL/2010, filed 9 Sep. 2010 in India, and which also claims benefit of Serial No. 1303/KOL/2009, filed 30 Oct. 2009 in India and which applications are incorporated herein by reference. To the extent appropriate, a claim of priority is made to each of the above disclosed applications.

TECHNICAL FIELD OF THE INVENTION

The present invention provides a novel process for preparation of darunavir that involves reduction of [(1S,2R)-3-[[(4-nitrophenyl)sulfonyl](2-methylpropyl)amino]-2-hydroxy-1-(phenylmethyl)propyl]carbamic acid (3R,3aS,6aR)-hexahydrofuro[2,3-b]furan-3-yl ester, of formula (5). The present invention is also related to darunavir ethanolate of fine particle size and process for its preparation.

BACKGROUND OF THE INVENTION

Darunavir is a potent HIV protease inhibitor belonging to the class of hydroxyethyl amino sulfonamides. Darunavir is known by chemical name [(1S,2R)-3-[[(4-aminophenyl)sulfonyl](2-methylpropyl)amino]-2-hydroxy-1-(phenylmethyl)propyl]carbamic acid (3R,3aS,6aR)-hexahydrofuro[2,3-b]furan-3-yl ester. Darunavir is generically disclosed in U.S. Pat. No. 5,843,946 and specifically disclosed in U.S. Pat. No. 6,248,775.

The ethanol solvate of darunavir, referred as Darunavir ethanolate is represented by following structure:

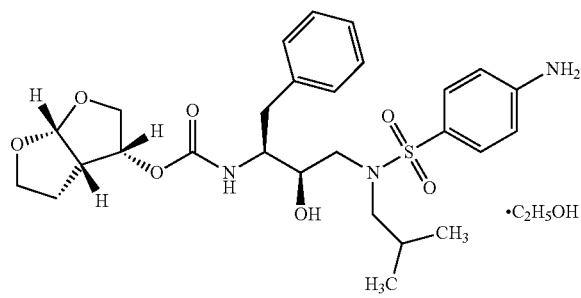

Darunavir ethanolate is marketed in USA by Tibotec Pharmaceuticals under the trade name Prezista® and is specifically covered by U.S. Pat. No. 7,700,645.

We observed that very few references are directed towards synthesis of darunavir. The product U.S. Pat. No. 6,248,775 B2 does not provide any enabling disclosure for preparation of darunavir (1).

The process described in the publication Dominique et. al; Journal of Medicinal Chemistry, 2005, 48(6), 1813-1822 and the patent application US 2007/060642 A1 which involves condensation of diamino compound (2) with furanyl derivative (3) is most relevant to the present invention and is depicted in scheme 1 below.

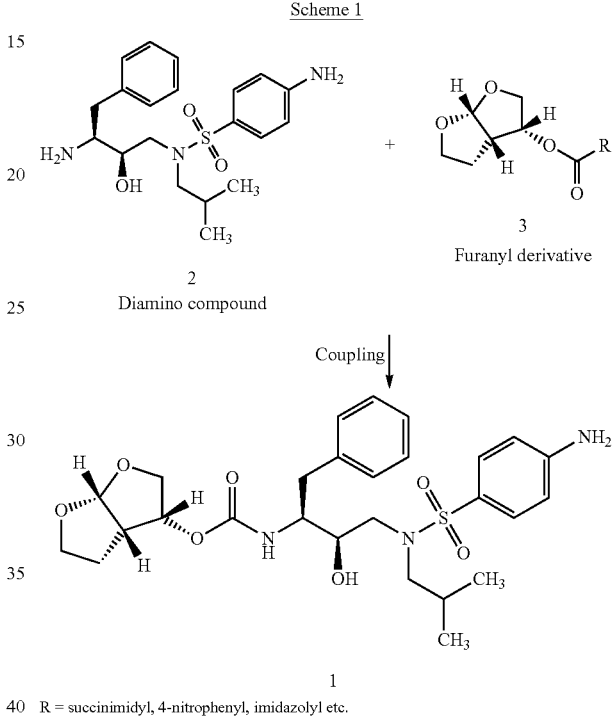

Scheme 1

R = succinimidyl, 4-nitrophenyl, imidazolyl etc.

The synthesis of darunavir (1) by coupling of diamino compound (2) with furanyl derivative (3) very likely leads to formation of impurities, viz., impurity A and impurity B. However, the formation of these impurities A and B is not mentioned in any of the prior art references.

The structural formulae of impurity A and impurity B are as represented below:

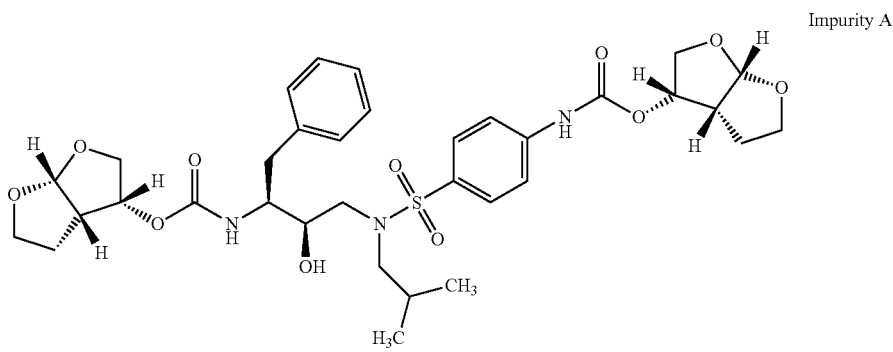

Impurity A

-continued

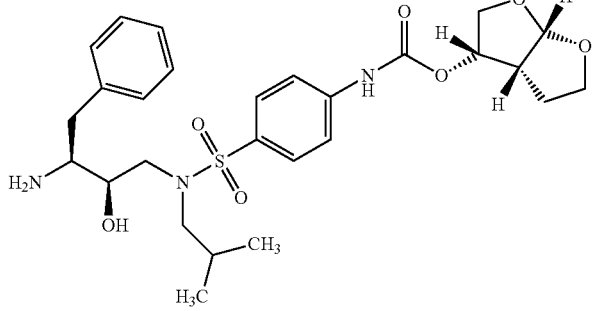

Impurity B

These impurities can form due to presence of 4-amino group in the 4-aminophenylsulfonyl group on the tertiary nitrogen of diamino compound (2), since it can react with furanyl derivative (3). Due to prevalence of these impurities the process of above mentioned prior art is less desired and there is a need to develop an improved process.

The publication Dominique et. al; Journal of Medicinal Chemistry, 2005, 48(6), 1813-1822 further discloses preparation of nitro compound (5) by reaction of amino compound (4) with furanyl derivative (3) (where R=succinimidyl group) in presence of triethylamine in tetrahydrofuran to obtain nitro compound (5). Surprisingly, this publication does not provide any suggestions for reduction of nitro compound (5) to obtain darunavir (1). The process disclosed in this publication is depicted in the synthetic scheme 2.

Scheme 2

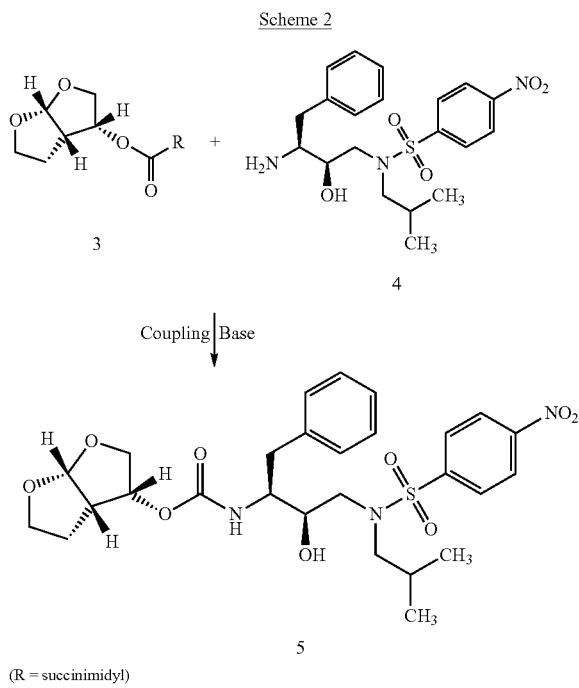

(R = succinimidyl)

The inventors of the present invention have developed a novel process, which not only avoids formation of impurities A and B but also performs reduction of nitro compound (5) under selective condition in such a way that decomposition of carbamate linkage occurs to a lesser extent.

It is well known that particle size can affect the solubility properties of a pharmaceutical compound. Particle size reduction can increase a compound's dissolution rate and consequently its bioavailability. Particle size can affect how freely the crystals or powdered form of the drug will flow past each other, which has consequence in production process of pharmaceutical products containing the drug. The inventors of the present invention have developed darunavir ethanolate of fine particle size, which has good solubility and is well suited for preparing pharmaceutical products.

SUMMARY OF THE INVENTION

The present invention provides a novel process for preparation of darunavir of formula (1), comprising the steps of:
 (i) condensation of the amino compound of formula (4) with furanyl derivative (3) to obtain nitro compound of formula (5);
 (ii) reduction of nitro compound of formula (5) to obtain darunavir; and
 (iii) optionally converting darunavir to darunavir ethanolate.

The present invention also provides darunavir ethanolate of particle size wherein $d_{0.9}$ is less than 130 μm, $d_{0.5}$ is less than 30 μm and $d_{0.1}$ is less than 10 μm. The present invention further provides a process for preparation of darunavir ethanolate of fine particle size comprising the steps of:
 (i) feeding darunavir ethanolate to milling chamber under nitrogen pressure;
 (ii) rotating the milling chamber; and
 (iii) collecting the smaller size particles.

DESCRIPTION OF THE INVENTION

The present invention provides a novel process for preparation of darunavir of formula (1)

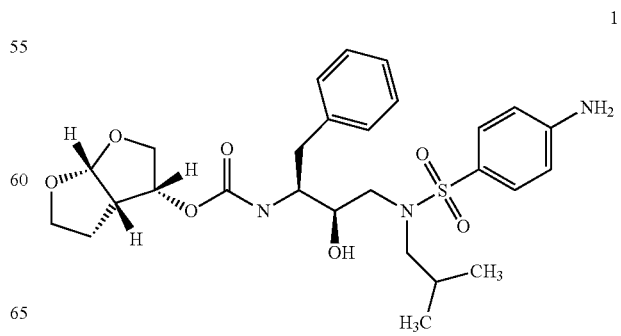

1 comprising the steps of:
(i) condensation of the amino compound of formula (4)

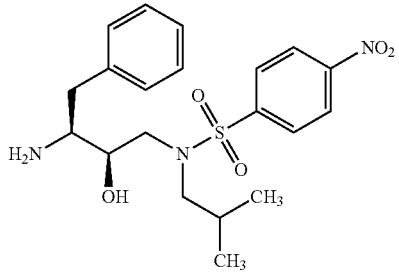

with furanyl derivative of formula (3)

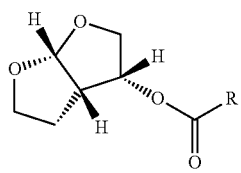

where R=succinimidyl, p-nitrophenyl, imidazolyl, phenyl, chloro or the like, to obtain nitro compound of formula (5);

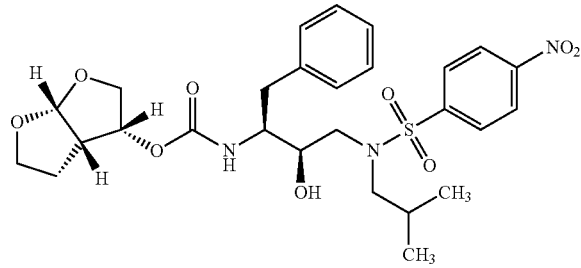

(ii) reduction of nitro compound of formula (5) to obtain darunavir (1); and
(iii) optionally converting darunavir (1) to darunavir ethanolate.

The process of present invention is depicted in scheme 3 given below

Scheme 3

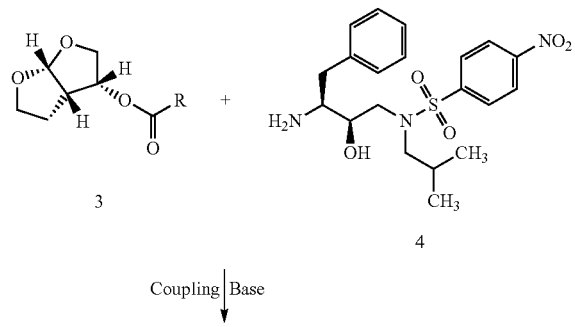

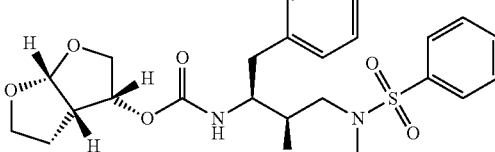

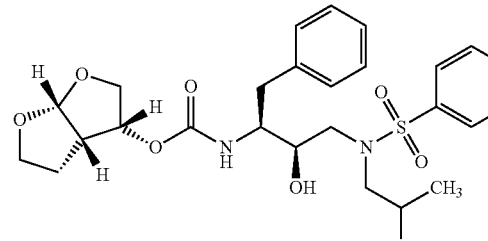

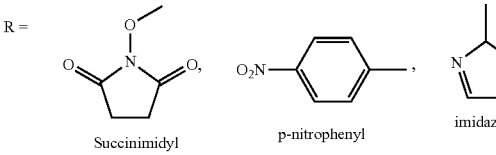

The starting compound (4) can be obtained by the methods known in U.S. Pat. No. 6,248,775 B2 and US 2007/060642 A1. The furanyl derivative (3) is obtained by reaction of (3R,3aS,6aR)hexahydrofuro[2,3-b]furan-3-ol of formula (6)

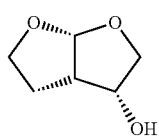

with succinimidyl carbonate, bis(4-nitrophenyl)carbonate, diimidazole carbonate, ter-butyloxycarbonyl anhydride, phenyl chloroformate, p-nitrophenyl chloroformate, phosgene etc.

The compound (3R,3aS,6aR)hexahydrofuro[2,3-b]furan-3-ol (6) employed for preparation of furanyl derivative (3) can be obtained by methods described in literature such as U.S. Pat. No. 6,919,465; WO 2008/055970 A2; WO 2005/095410 A1; WO 03/022853 A1; Dominique et. al, Journal of Medicinal Chemistry, (2005), 48(6), 1813-1822; Ghosh et. al, Journal of Organic Chemistry, (2004), 69(23), 7822-7829; Ghosh et. al, Journal of Medicinal Chemistry, (1996), 39, 3278-3290; Ghosh et. al; Tetrahedron Letters, (1995), 36(4), 505-508.

In one embodiment, the present invention provides a process for preparation of darunavir by carrying out coupling of the amino compound (4) with furanyl derivative (3) in a solvent or mixture of solvents in presence of a base to obtain the nitro compound (5).

The molar equivalent of furanyl derivative (3) with respect to amino compound (4) is in the range of 0.8 to 3, preferably 1.0 to 1.2.

The coupling is carried out in a solvent selected from lower alcohols such as methanol, ethanol, n-propanol, isopropanol; ketones such as acetone, ethylmethyl ketone, diethyl ketone, methylisobutyl ketone; lower aliphatic esters such as ethyl acetate, methyl acetate; halogenated hydrocarbons such as dichloromethane, chloroform dichloroethane; dimethylformamide, dimethyl sulfoxide, acetonitrile, water or mixtures thereof. Most preferably dichloromethane is used as a solvent for coupling reaction.

The coupling reaction is carried out in presence of an organic or inorganic base. The organic base is selected from triethylamine, diisopropylethyl amine, pyridine and the like while inorganic base is selected from hydroxides of alkali metals or alkaline earth metals such as sodium hydroxide, potassium hydroxide, lithium hydroxide; bicarbonates of alkali metals or alkaline earth metals such as sodium bicarbonate, potassium bicarbonate and the like; carbonates of alkali metals or alkaline earth metals such as sodium carbonate, potassium carbonate; ammonia or the like. Most preferably triethylamine is used as a base.

The molar ratio of base with respect to amino compound (4) is in the range of 0.5 to 6 molar equivalents, more preferably 1 to 3 molar equivalents, most preferably 2 molar equivalents.

The coupling reaction is carried out at a temperature ranging from −20° C. to 100° C., more preferably in range of 0° C. to 50° C., most preferably at 20-30° C.

In another preferred embodiment, the present invention provides a novel process for reduction of the nitro compound (5) in an organic solvent or mixture of solvents in presence of a transition metal catalyst to obtain darunavir.

Solvent suitable for reduction of the nitro compound (5) may be selected from lower alcohols such as methanol, ethanol, isopropyl alcohol, ter-butyl alcohol; aliphatic esters such as ethyl acetate, methyl acetate, isopropyl acetate; amides such as dimethyl formamide; aliphatic halogenated hydrocarbons such as dichloromethane, chloroform; aromatic hydrocarbons such as benzene, xylene, toluene; ethers such as diethyl ether, diisopropyl ether, tetrahydrofuran, 1,4-dioxane; dimethylsulfoxide, water or any mixtures thereof. More preferably esters such as ethyl acetate, methyl acetate, isopropyl acetate are used, most preferably ethyl acetate is employed.

The catalyst employed for reduction is selected from transition metal catalyst such as palladium on carbon, $PtO_2$, Raney Nickel, ruthenium, rhodium; iron in acidic medium; borane complexes, diborane; borohydrides such as sodium borohydride, lithium aluminium hydride and the like.

The reduction of the nitro compound (5) is more preferably carried out by catalytic hydrogenation in presence of transition metal catalyst selected from palladium on carbon, $PtO_2$ and Raney nickel. Palladium on carbon is most preferred amongst these.

The hydrogenation is carried out at a temperature ranging from −20° C. to 100° C., more preferably in range of 0° C. to 50° C., most preferably at 20-30° C.

The reduction of nitro moiety is optionally carried out in presence of an organic or inorganic base. The organic base is selected from triethylamine, diisopropylethyl amine, pyridine and the like while inorganic base is selected from hydroxides of alkali metals or alkaline earth metals such as sodium hydroxide, potassium hydroxide, lithium hydroxide; bicarbonates of alkali metals or alkaline earth metals such as sodium bicarbonate, potassium bicarbonate and the like; carbonates of alkali metals or alkaline earth metals such as sodium carbonate, potassium carbonate; ammonia or mixtures thereof. Most preferably triethylamine is used as a base.

The molar ratio of base with respect to nitro compound (5) is in the range of 0.5 to 5 molar equivalents, more preferably 1 to 3 molar equivalents, most preferably 1.5 molar equivalents.

The process of present invention has following advantages over the prior art method:
1. It employs condensation of amino compound (4) with the furanyl derivative (3), which avoids formation of impurity A and impurity B.
2. The reduction of nitro compound (5) by catalytic hydrogenation is preferably carried out in basic condition, which prevents cleavage of the carbamate linkage.
3. Better yield of darunavir.
4. Enhanced purity of darunavir.

In another aspect the invention provides darunavir ethanolate having particle size wherein $d_{0.5}$ is less than 30 µm.

In yet another aspect the invention provides darunavir ethanolate having particle size wherein $d_{0.9}$ is less than 130 µm and $d_{0.5}$ is less than 30 µm.

In yet another aspect the invention provides darunavir ethanolate having particle size wherein $d_{0.9}$ is less than 130 µm, $d_{0.5}$ is less than 30 µm and $d_{0.1}$ is less than 10 µm.

Comminution of darunavir ethanolate may be performed by any of the known methods of particle size reduction. The principal operations of conventional size reduction are milling of a feedstock material and sorting of the milled material by size.

Micronization is carried out by known methods such as jet milling, media milling, pulverization and the like. Preferably micronization is carried out in a jet mill type micronizer.

In another embodiment, the present invention provides a process for preparation of darunavir ethanolate having fine particle size comprising the steps of:
(i) feeding darunavir ethanolate to milling chamber under nitrogen pressure;
(ii) rotating the milling chamber; and
(iii) collecting the smaller particles.

Darunavir ethanolate employed could be in the form of crystals, powdered aggregates and coarse powder of either crystalline or amorphous form.

All the steps of above mentioned micronization process are performed at ambient temperature. The feedstock of solid particles of darunavir ethanolate is tangentially fed in to the circular milling chamber. Milling chamber is rotated at a speed of 10-50 rpm, more preferably at 20-30 rpm for a time period of 1-10 hours, preferably for 3-7 hours. Milling chamber is supplied with nitrogen under pressure of approximately 1-5 $Kg/cm^2$, more preferably 2-3 $Kg/cm^2$. The particles are accelerated in a spiral movement in the milling chamber by number of angular holes in the ring and deposited on the periphery of the chamber. The milling action takes place due to high velocity of nitrogen. Larger particles get retained at the periphery due to centrifugal force and smaller particles travel along with the exhaust nitrogen through central port and get collected in the collection chamber.

The particle size of the darunavir ethanolate obtained by the process of present invention can be determined by any method known in the art such as laser diffraction, sieve analysis, microscope observation, sedimentation etc. Malvern mastersizer is an instrument employed for particle size determination in the present invention.

The invention is further defined by reference to the following examples. It is apparent to those skilled in the art that many modifications, both to materials and methods, may be practiced without departing from scope of the invention.

Example 1

Separation of Nitro Compound (5)

The solution of 3.5 g (0.013 mol) of furanyl derivative (3) in a mixture of 50 ml of dichloromethane and 50 ml of acetonitrile was cooled to 0-5° C. and 1.98 ml (0.014 mol) of triethylamine was added. To the mixture 5 g (0.011 mol) of amino compound (4) was added and stirred for 1 hour. The reaction mixture was warmed to room temperature. To the reaction mixture 0.2 g of 40% aqueous solution of methyl amine was added and was heated till completion of the reaction. The reaction mixture was washed twice with 10% sodium carbonate solution (25 ml×2) and layers were separated. The organic layer was washed with water, dried over sodium sulfate and evaporated to dryness under vacuum. The residue was recrystallized from 50 ml ethanol and dried under vacuum at 40-45° C.

Yield=5.8 g

Example 2

Preparation of Darunavir

The solution of 5 g (0.009 mol) of nitro compound (5) in 100 ml of ethyl acetate was prepared by warming and cooled to room temperature. To the solution 2.5 ml (0.018 mol) of triethylamine and 0.5 g of 10% Pd/C (50% wet) were added. Hydrogenation was carried out at 3 Kg pressure for 1-2 hours at room temperature. Catalyst was filtered off and washed with 10 ml ethyl acetate. Solvent was evaporated under reduced pressure to obtain residue. To the residue 110 ml isopropyl alcohol was added and heated to 70-75° C. to obtain clear solution. It was cooled to room temperature and stirred for 1 hour. The crystals obtained were filtered, washed with isopropyl alcohol and dried under vacuum.

Yield=4.7 g

Example 3

Preparation of Darunavir Ethanolate 100 gm of darunavir was dissolved in 1000 ml of denatured ethanol (mixture of 97% ethanol and 3% toluene) at 70-75° C. to obtain clear solution. 5 gm of activated charcoal was added and stirred for 120-150 minutes. The hot solution was filtered through hyflow bed and the bed was washed with 100 ml ethanol. The solution was filtered again through 0.2μ filter maintaining temperature at 70-75° C. The reaction mass was cooled to 15-20° C., stirred for an hour and filtered. The wet cake was washed with 100 ml of chilled ethanol and dried under vacuum at 40-45° C. to afford 89.5 gm of off white colored crystalline solid.

Example 4

Preparation of Darunavir Ethanolate of Fine Particle Size 37.3 Kg of darunavir ethanolate obtained as per process described in example 1 was tangentially fed in to the circular milling chamber of the jet mill micronizer through a venturi under nitrogen at a pressure of about 2 Kg/cm$^2$. The milling chamber was rotated at a speed of 28 rpm at ambient temperature for 3-7 hours. The smaller particles were collected in the collection chamber.

Yield=0.99 Kg (w/w)

Particle size distribution: $d_{0.9}$=97 μm; $d_{0.5}$=18 μm; $d_{0.1}$=2 μm

Purity (by HPLC assay)=99.7%

Bulk density=0.42 g/ml

Tapped density=0.72 g/ml

Any other individual impurity was below detection limit (by HPLC).

The invention claimed is:

1. Darunavir ethanolate having particle size wherein D90 is less than 130 μm, D50 is less than 30 μm and D10 is less than 10 μm.

2. A process for preparation of darunavir ethanolate of claim 1, comprising the steps of:
    (i) feeding darunavir ethanolate to milling chamber under nitrogen pressure;
    (ii) rotating the milling chamber; and
    (iii) collecting the smaller particles.

3. The process according to claim 2, wherein step (i) is performed at nitrogen pressure of about 1-5 Kg/cm$^2$.

4. The process according to claim 3, wherein step (i) is performed at nitrogen pressure of 2-3 Kg/cm$^2$.

5. The process according to claim 2, wherein step (ii) is performed at 10-50 rpm.

6. The process according to claim 5, wherein step (ii) is performed at 20-30 rpm.

* * * * *